United States Patent [19]
de Jaeger et al.

[11] Patent Number: 5,498,551
[45] Date of Patent: *Mar. 12, 1996

[54] METHOD FOR THE DETECTION OF SPECIFIC BINDING AGENTS AND THEIR CORRESPONDING BINDABLE SUBSTANCES

[75] Inventors: Nikolaas C. J. de Jaeger, Hove; Marcel J. Monbaliu, Mortsel; Marcus J. M. Noppe, Kalmthout; Frank J. Konings, Antwerpen, all of Belgium

[73] Assignee: Janssen Pharmaceutica N.V., Beerse, Belgium

[*] Notice: The term of this patent shall not extend beyond the expiration date of Pat. No. 4,837,168.

[21] Appl. No.: 243,425

[22] Filed: May 16, 1994

Related U.S. Application Data

[63] Continuation of Ser. No. 8,858, Jan. 25, 1993, abandoned, which is a continuation of Ser. No. 345,755, May 1, 1989, abandoned, which is a continuation of Ser. No. 941,446, Dec. 15, 1986, Pat. No. 4,837,168, which is a continuation-in-part of Ser. No. 812,586, Dec. 23, 1985, abandoned.

[51] Int. Cl.$^6$ .................................................. G01N 33/546
[52] U.S. Cl. ..................... 436/533; 428/403; 436/534; 436/800; 436/805; 436/823
[58] Field of Search ..................... 436/533, 534, 436/800, 805, 823; 428/403

[56] References Cited

U.S. PATENT DOCUMENTS

| | | | |
|---|---|---|---|
| 4,340,664 | 7/1982 | Monbaliu et al. | 430/449 |
| 4,369,226 | 1/1983 | Rembaum | 428/334 |
| 4,419,453 | 12/1983 | Dorman et al. | 436/534 |
| 4,703,017 | 10/1987 | Campbell et al. | 436/534 |
| 4,745,075 | 5/1988 | Hadfield et al. | 436/533 |

FOREIGN PATENT DOCUMENTS

| | | |
|---|---|---|
| 0032270 | 12/1980 | European Pat. Off. . |
| 0170746 | 8/1984 | European Pat. Off. . |
| 0154749 | 12/1984 | European Pat. Off. . |
| 1130581 | 6/1964 | United Kingdom . |
| 1247688 | 2/1968 | United Kingdom . |
| 1269355 | 7/1968 | United Kingdom . |
| WO84/03358 | 8/1984 | WIPO . |

*Primary Examiner*—Mary E. Ceperley

[57] ABSTRACT

New method for the detection of specific binding agents and their corresponding bindable substances by employing a label which is a latex particle which can be visually detected.

12 Claims, No Drawings

METHOD FOR THE DETECTION OF SPECIFIC BINDING AGENTS AND THEIR CORRESPONDING BINDABLE SUBSTANCES

This application is a continuation of application Ser. No. 008,858 filed Jan. 25, 1993, now abandoned; which is a continuation of application Ser. No. 345,755, filed May 1, 1989, now abandoned; which is a continuation of application Ser. No. 941,446, filed Dec. 15, 1986, now U.S. Pat. No. 4,837,168, which is a continuation in part of application Ser. No. 812,586, filed Dec. 23, 1985, now abandoned.

BACKGROUND OF THE INVENTION

Various methods are presently used for the detection and/or quantitative determination of specific binding agents and/or their corresponding bindable substances. Although these methods differ greatly from each other in sensitivity, ease of operation and chemical and physical principles involved, important similarities are generally recognized. Mostly, the relationship between a specific binding agent and its corresponding bindable substance(s) will be of the acceptor-ligand type, such as, for example, antigen-antibody and receptor-ligand interactions. Antigen-antibody or immunological interactions are by far the most important in this connection, and, particularly for diagnostic purposes, detection methods based on such interactions are the most widely used today.

Various techniques can be employed to detect and optionally quantify the complexes formed between the specific binding agents and bindable substances involved. In certain instances, the complexation reaction will lead to a directly visible signal as a result of agglutination and/or precipitation of the complex itself. This will however not always be the case and, in general, the concentration of binding protein and bindable substance needed to produce such result will be far above the practical and useful limits. In order to circumvent this lack of sensitivity or to detect otherwise undetectable complexes, various methods have been developed such as, for example, immunodiffusion, immuno-electrophoresis, complement fixation, passive haemagglutination, radio-immuno assay (RIA), immuno-fluorescence, enzyme-linked immuno sorbent assay (ELISA). In the last three methods, the detection of the complex is facilitated by labelling the complex with an easily detectable marker which is either bound directly to the specific binding protein, to a secondary binding protein for which the primary binding protein acts as a bindable substance, or to the bindable substance. In the three methods listed, the marker is respectively a radioactive atom or group, a fluorescent substance or an enzyme. Such methods are described i.a. in Weir's Handbook of Experimental Immunology (1967), Blackwell Scientific Publications, Oxford and Edinburgh and U.S. Pat. No. 3,654,090 (ELISA).

More recently, methods have been developed wherein the complexes formed between specific binding protein and bindable substance are visualized by labelling the said complexes directly or indirectly with colloidal metal particles, particularly gold particles. Depending on the circumstances, these particles can be dectected e.g. by direct visual examination, by microscopic or spectrofotometric techniques. A description of the "sol particle immuno assay" (SPIA) technique and of specific applications and improvements thereof will be found e.g. in U.S. Pat. Nos. 4,313,734, 4,446,238 and 4,420,558.

Use has also been made of a latex agglutination method as described e.g. in U.S. Pat. No. 3,857,931 which has certain advantages over the haemagglutination method mentioned above. Indeed, the red blood cell carriers are themselves antigenic and often cause specific agglutination which interferes with the desired antigen-antibody reaction and renders the efficiency of the determination to a large extent dependent on the nature and composition of the material under analysis. The synthetic polymer latexes employed are devoid of this disadvantage. However, their sensitivity is in general insufficient.

The method according to the present invention differs from the previous methods essentially by the fact that as a marker to detect or determine the complex formed between a specific binding protein and the corresponding bindable substances there are used latex particles which can be detected visually due to their capability to absorb light in the visual spectrum, or to emit light after irradiation. The former detection is based on colour, the latter on fluorescence.

DESCRIPTION OF THE INVENTION

The present invention is concerned with a method of qualitatively or quantitatively determining a component of a complex formed between at least one specific binding agent, which preferably is a specific binding protein, and its corresponding bindable substance. Said method comprises labelling at least one component of said complex with a marker which is easier to determine than the complex itself, whereby the marker used consists of latex particles which can be detected visually due to their capability to absorb light in the visual spectrum, or to emit light after irradiation, the former detection being based on colour, the latter on fluorescence. Preferably the marker consists of coloured or colourable latex particles and the determination is based on the colour characteristics of the latex particles as such or, in the instance that colourable latex particles are used, on the colour characteristics of the coloured particles derived therefrom.

The colour, respectively fluorescence signal is, if necessary after development, easily detected and optionally quantified. The method is essentially based on the fact that the specific binding agents or any agents bindable thereby, when brought into contact with the latex particles under appropriate conditions, do strongly adsorb thereon without loosing their affinity for their binding or bindable counterpart and that the signal density of the particles is sufficient to allow the detection and/or quantification of small concentrations and amounts. Hence, the thus labelled specific binding agents or bindable agents, when allowed to interact with their counterparts will attach their label to the complex formed during the interaction and consequently the detection thereof can be easily performed making use of the optical properties of the latex particles, especially of their fluorescence and colour characteristics.

The latex particles for use in the method according to the invention are meant to include any aqueous dispersion of synthetic homopolymers or copolymers containing moieties which can, if necessary after development, absorb light in the visual spectrum or emit light after irradiation. The said moieties can either be covalently bound to the polymers, e.g. the polymers comprise recurring units carrying such a moiety, or can be incorporated in the latex particles, e.g. when a molecule containing such a moiety is solvatated in the latex particle.

Preferably the latex particles for use in the method according to the present invention are detectable on basis of their colour. Particularly preferred latex particles are those wherein the colour is due to recurring units carrying a light absorbing moiety or which can be chemically converted into such moiety, e.g. by the oxidative coupling of the latter with an aromatic primary amino compound to form a dye.

Examples of coloured and colourable latexes are well-known in the art and comprise, for example, homo- or copolymers of metacrylamide units wherein the amide nitrogen atom is chemically bound to a coloured or colourable residue. Typical examples of metacrylamide monomers carrying a coloured residue and their preparation will be found e.g. in Shih, Yen Jet, "COLORED LATEXES: PREPARATION, CHARACTERIZATION AND APPLICATION", Lehigh University (1981). A typical preparation comprises an emulsion polymerization of styrene monomer, seeded polymerization with reactive halogenated monomer, amination with N-methylaniline and a coupling reaction with a diazonium salt, e.g. a benzenesulfonate diazonium salt. Instead of diazo groups, the coloured latexes may contain different chromophores, such as, for example, anthraquinone residues. Colourable latexes which can be used in accordance with the present invention include, e.g., the various types of colour complex latexes used in photographic colour film. These are homo- or co-polymers comprising recurring units carrying a moiety capable of oxidatively coupling with an aromatic primary amino compound to form a dye. In particular the polymer carries recurring units of a monomer which can be represented by the following general formula

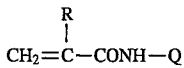

wherein:

R is hydrogen, halogen or $C_{1-4}$ alkyl;

Q is a colour coupler group capable of oxidatively coupling with an aromatic primary amino compound, e.g. of the p-phenylene diamine type; in particular Q is a coupler group of the phenol or naphthol type, of the pyrazolone or indazolone or of the acylacetamide type.

Colour couplers are well known in the art of silver halide photography. The monomers represented by the above formula may comprise as group Q:

1. a group of a cyan-forming colour coupler of the phenol or naphthol type e.g. within the scope of the following general formula (I):

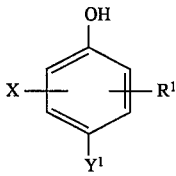

wherein:

X is a single chemical bond or a bivalent organic group linking the ethylenically unsaturated group to the colour coupler group, $R^1$ represents hydrogen, a substituent of the type used in phenol or naphthol colour couplers e.g. halogen, alkyl or aryl, aminoacyl or the atoms necessary to complete a fused-on benzene nucleus, which may be substituted, and $Y^1$ represents a hydrogen atom or a substituent that splits off upon oxidative coupling, for example, a halogen atom, e.g. chlorine, an acyloxy group, an alkoxy, aryloxy, or heterocycloxy group, an alkylthio, arylthio, or heterocyclic thio group, e.g. a tetrazolylthio group or a phenylazo group.

2. a group of a magenta-forming colour coupler of the pyrazolone or indazolone type e.g. within the scope of the following general formula

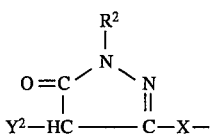

wherein:

$R^2$ is a substituent of the type used in the 1-position of 2-pyrazolin-5-on colour couplers, e.g. alkyl or substituted alkyl, e.g. haloalkyl such as fluoroalkyl, cyanoalkyl and benzyl; aryl or substituted aryl e.g. phenyl, which may be substituted with alkyl, halogen, e.g. trichlorophenyl, alkoxy, or haloalkylthio; or a N-heterocyclic substituent e.g. 2-oxazolyl, 2-thiazolyl and the like;

$Y^2$ is hydrogen or a substituent that splits off upon oxidative coupling, for example, a halogen atom, e.g. chlorine, an acyloxy group, an alkoxy group, an aryloxy group, or a heterocycloxy group, an aryloxy group, or a heterocycloxy group, an alkylthio group, an arylthio group, a heterocyclic thio group, e.g. a tetrazolylthio, a phenylazo group; or a N-heterocycle, e.g. 1-triazolyl, benzotriazolyl, 1H-imidazol-1-yl and the like.

X has the same meaning as in formula (I).

3. a group of a yellow-forming colour coupler of the acylacetamide type, especially the acylacetanilide type e.g. an anilino-carbonylacetophenyl group or a benzoylacetamidophenyl group, wherein both aryl groups may be substituted by substituents well-known in yellow-forming colour couplers, e.g. alkyl, alkoxy, halogen, alkylthio or alkylsulfonyl, and wherein the active methylene group may carry a substituent that is split off upon oxidative coupling, for example, a halogen atom, e.g. chlorine, acyloxy, an alkoxy, aryloxy, or heterocycloxy group, an alkylthio, arylthio, heterocyclic thio or N-heterocyclic group, e.g. 1,3-dimethyl-2,6-dioxo-7-purinyl (theophyllinyl) and the like.

Examples of monomeric colour couplers used according to the present invention can be found e.g. in the Belgian Patent Specifications 584,494, 602,516 and 669,971, in the United Kingdom Patent Specifications 967,503, 1,130,581; 1,247,688; 1,269,355; and in the U.S. Patent Specification 3,356,686.

Representative examples of monomeric colour couplers are:

2-methylsulfonylamino-5-methacrylaminophenol;
2-methylsulfonylamino-4-chloro-5-methacrylaminophenol;
2-phenylsulfonylamlno-5-methacrylaminophenol;
2-(4-chlorophenyl)sulfonylamino-5-methacrylaminophenol;
2-(4-sec.butylphenyl)sulfonylamino-5-methacrylaminophenol;
2-ethoxycarbonylamino-5-methacrylaminophenol;
2-n.butylureido-5-methacrylaminophenol:
2-benzoylamino-5-methacrylaminophenol:
2-o-methylbenzoylamino-5-methacrylaminophenol;
2-acetylamino-5-methacrylaminophenol;
2-p-methylbenzoylamino-5-methacrylaminophenol;
2-o-chlorobenzoylamino-5-methacrylaminophenol:
2-p-t.butylbenzoylamino-5-methacrylaminophenol;
1-hydroxy-N-β-acrylamidoethyl-2-naphthamide;
1-hydroxy-N-β-vinyloxyethyl-2-naphthamide;
1-hydroxy-4-chloro-N-β-methacrylamidoethyl-2-naphthamide;
1-hydroxy-4-chloro-N-β-acrylamidoethyl-2-naphthamide;
2-methylacrylamido-4,6-dichloro-5-methylphenol;
1-benzyl-3-acrylamido-2-pyrazolin-5-one;
1-(2-cyanoethyl)-3-methacrylamido-2-pyrazolin-5-one;
1-(3,4-dichlorobenzyl)-3-methacrylamido-2-pyrazolin-5-one;

1-(2,2-trifluoroethyl)-3-methacrylamido-2-pyrazolin-5-one;
1-phenyl-3-methacrylamido-2-pyrazolin-5-one;
1-o-bromophenyl-3-methacrylamido-2-pyrazolin-5-one;
1-(2',4',6'-trichlorophenyl)-3-acrylamido-2-pyrazolin-5-one:
p-methacrylamidobenzoylacetanilide:
3-methoxy-4-(9-methoxybenzoylacetylamino)-methacrylanilide;
p-methacrylamido-benzoylacetaniside; and
2-chloro-4-methacrylamido-benzoylacetanilide.

The polymeric compounds, e.g. polymeric couplers for use according to the present invention, can be characterized by their so-called equivalent molecular weight. By equivalent molecular weight is understood the number of grams of polymer containing 1 mole of polymerized monomeric compound with chemically reactive moiety, e.g. monomeric coupler. It can be compared with the molecular weight of the non-polymeric classical non-migratory chemically reactive compound, e.g. coupler. The equivalent molecular weight of polymeric latex compounds according to the invention can vary within very wide limits, preferable from 200 to 2000.

The latexes used in the present invention can be prepared by emulsion polymerization using a polymerization initiator as described e.g. in the U.S. Patent Specification 3,926,436 and United Kindom Patent Specification No. 1,130,581.

Examples of polymerization initiators suitable for use in the emulsion polymerization process are e.g. persulfates such as ammonium and potassium persulfate, azonitrile compounds such as 4,4'-azo-bis(4-cyanovaleric acid) and likewise peroxide compounds e.g. benzoylperoxide.

The aqueous dispersion of the present polymer particles i.e. the latex for use in the method according to the present invention may contain conventional emulsifiers.

Emulsion polymerisation methods of a solid water-insoluble monomer coupler in water are described in U.S. Pat. No. 4,080,211 and Belgian Pat. No. 669,971.

A first polymerization method comprises dissolving a solid water-insoluble monomer coupler in an ethylenically unsaturated copolymerizable monomer and an organic solvent which may be completely water-miscible or poorly water-miscible, then adding the resulting solution to an aqueous reaction medium containing an emulsifier and initiating polymerization. The organic solvent suited for use in this method however, must satisfy the following requirements: (1) it is substantially inert to the solid water-insoluble monomer coupler, (2) it does not interrupt the normal action of the free-radical addition polymerization, and (3) it has a low boiling point which makes it possible to easily remove it from the aqueous reaction medium by distillation during and/or after the polymerization.

The poorly water-miscible solvent has preferably a boiling point of at most 130° C. and a sufficiently high vapour pressure so that it can still be removed readily from the aqueous dispersion by applying a vacuum of 665 to 15 mbar at a temperature of 25° to 80° C. Examples of suitable solvents are methylene chloride, ethyl formate, n-butyl formate, ethyl acetate, n-propyl acetate, isopropyl acetate, butyl acetate, methyl propionate, ethyl propionate, diethyl carbonate, carbon tetrachloride, sym. tetrachloroethane, 1,1,2-trichloroethane, 1,2-dichloropropane, chloroform, ethanol, n-butanol, diethyl ketone, methyl n-propyl ketone, diisopropyl ether, cyclohexane, methyl cyclohexane, benzene, toluene and nitromethane.

A second polymerization method comprises dissolving a solid water-insoluble monomer coupler in an ethylenically unsaturated copolymerizable monomer, then adding the resulting solution to an aqueous reaction medium containing an emulsifier and a substance initiating polymerization.

A third polymerization method comprises dispersing a solid water-insoluble monomer coupler and an ethylenically unsaturated copolymerizable monomer or a solid water-insoluble monomer coupler, an ethylenically unsaturated copolymerizable monomer and an organic solvent in an aqueous reaction medium containing an emulsifier and a substance initiating polymerization.

In an embodiment for the preparation of a latex used according to the present invention the hydrophobic monomer is dispersed in the absence of an organic solvent so that no such solvent has to be removed from the eventually obtained latex. It may be advantageous, however, particularly when the dispersion proceeds with difficulty, to dissolve the monomer first in said already mentioned poorly water-miscible organic solvent(s) and to remove the solvent(s) later on.

The preparation of polymer coupler latexes including latex-particles having a layered structure is described in U.S. Pat. No. 4,444,870. Said preparation proceeds as follows:
(a) at least one ethylenically unsaturated monomer which does not have an ability of oxidative coupling with an aromatic primary amine developing agent is subjected to emulsion polymerization to prepare a polymer latex in a first state polymerization, and then
(b) a monomer coupler capable of forming a dye upon coupling with an oxidation product of an aromatic primary amine developing agent and at least one non-colour forming ethylenically unsaturated monomer and subjected to emulsion polymerization in an aqueous reaction medium containing an organic solvent in a second stage polymerization. Other techniques for the preparation of polymer coupler latexes are described in U.S. Pat. No. 3,767,412.

In addition to the repeating units derived from the monomers comprising a coloured moiety or a chemically reactive moiety capable of forming a coloured moiety the latex polymer of the present invention comprises still other repeating units that are colourless. These repeating units are derived e.g. from a monomer or mixture of monomers providing particular physical characteristics to the latex e.g. improved thermal stability, and improved compatibility with hydrophilic binders e.g. gelatin. Colourless ethylenically unsaturated monomers that are chemically inert in the sense as defined and that are copolymerisable with the monomers according to general formula (I) are e.g. acrylic acid, methacrylic acid and esters and amides derived from these acids, α-chloroacrylic acid, α-alkacrylic acids, wherein the substituting alkyl contains from 1 to 4 carbon atoms e.g. methyl, ethyl, and n-propyl, the esters and amides derived from acrylic acid, α-chloroacrylic acid and these α-alkacrylic acids, such as acrylamide, methacrylamide, ethyl acrylate, n-butyl acrylate, 2-ethylhexyl acrylate and lauryl methacrylate, vinyl esters such as vinyl acetate, vinyl propionate, and vinyl laurate, acrylonitrile, methacrylonitrile, aromatic vinyl compounds and derivatives thereof such as styrene and its derivatives, e.g. vinyl toluene, vinyl acetophenone and sulfostyrene, iraconic acid, citraconic acid, crotonic acid, vinylidene chloride, vinyl alkyl ethers such as vinyl ethyl ether, maleic acid esters, N-vinyl-2-pyrrolidone, N-vinylpyridines e.g. 2- and 4-vinyl-pyridine and ethylenically unsaturated monomers such as 2-acetoacetoxyethylmethacrylate.

The stability of the latexes used according to the invention may be improved by structural units of an ionogenic comonomer containing at least one long hydrophobic group, e.g. containing at least 8 carbon atoms, and of a strong hydrophilic group, e.g. sulfonic acid, sulfuric acid or phosphonic acid group or salt thereof.

Due to the presence of said ionogenic comonomer the activity of the chemically reactive moiety in the other comonomer for colour formation is raised in aqueous processing which is clearly demonstrated in the formation of a dye in a higher concentration and improved reaction speed when using a comonomer with colour coupler group copolymerised with said ionogenic comonomer.

Representative examples of ionogenic monomers are described in U.S. Pat. No. 4,340,664 and correspond to the following structural formulae:

1.

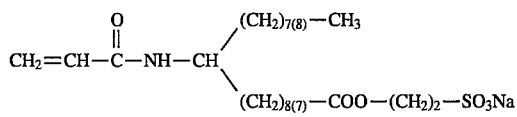

2.

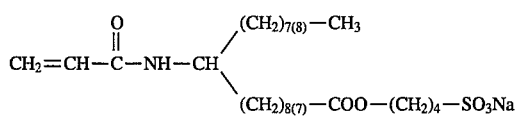

3.

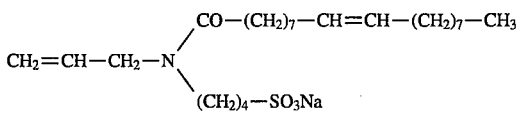

4.

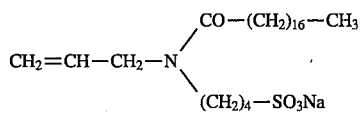

5.

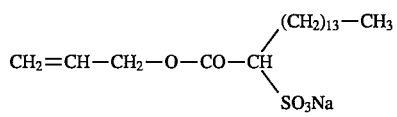

6.

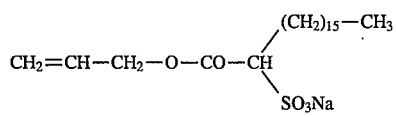

7.

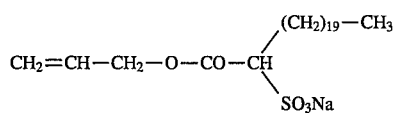

8.

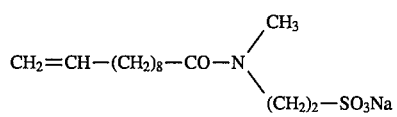

9.

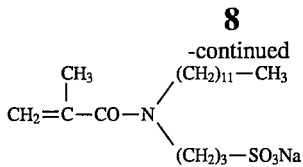

10.

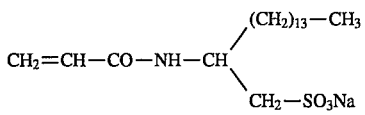

11.

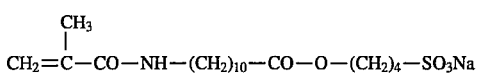

12.

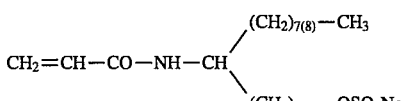

13.

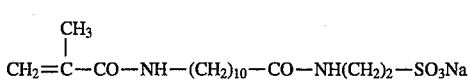

14.

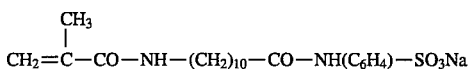

The particle size of the latexes prepared with the monomers is generally smaller than 100 nm, in most cases smaller than 70 nm.

The preferred colourable latex particles to be used according to the method of the present invention comprise a polymer selected from the group consisting of a polymer of formula

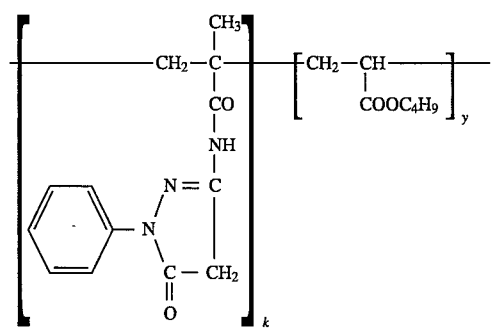

wherein k is from 30 to 60 and y is from 40 to 70 w/w: a polymer of the formula

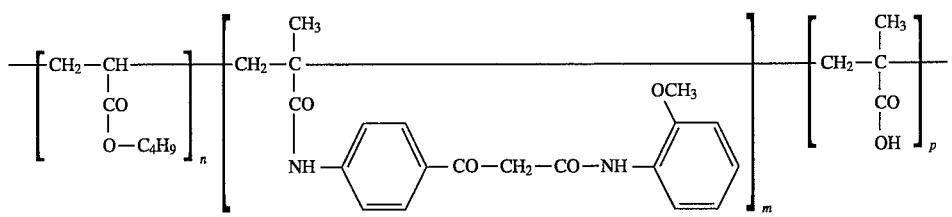

wherein n is from 20 to 70, m is from 30 to 60, and p is from 0 to 40 a polymer of the formula

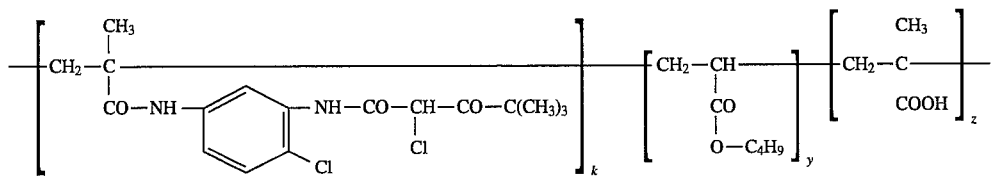

wherein k is from 30 to 60, y is from 20 to 70, and z is from 0 to 40; a polymer of the formula

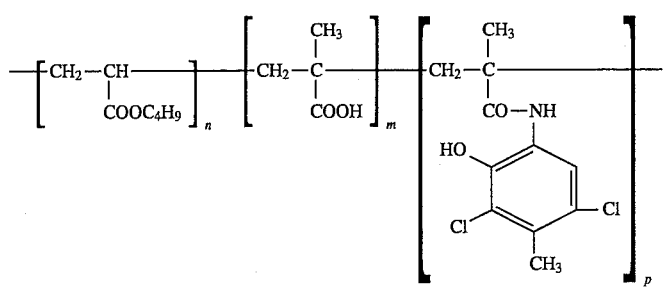

wherein n is from 20 to 70, m is from 0 to 40. and p is from 30 to 60; and a polymer of the formula

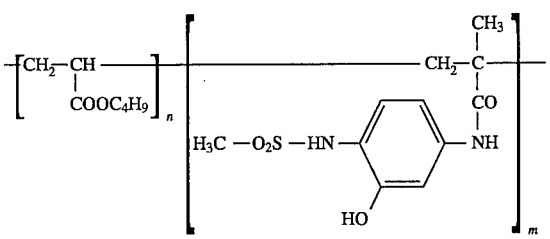

wherein n is form 40 to 70 and m is from 30 to 60.

As used in the previous formulae the numbers represented by the symbols k, y, n, m, p and z are precentages by weight.

Surface-active agents, e.g. anionic, cationic and non-ionic surface active agents, which are useful in the dispersing of non-self-dispersing monomers may be used too in the dispersing of the hydrophobic substance to be incorporated and/or adsorbed to the latex particles. Such substances are described e.g. in U.S. Pat. No. 3,912,517.

The labelling of the specific binding agents or preferably of the specific binding proteins with the coloured or colourable latex particles is easily carried out following the methodologies used for the coating of plastics with proteins, including antibodies. In general, the coating is easily effected by contacting the particles in an aqueous medium of appropriate pH wherein the desired proteins are dissolved. After a suitable period of time, the excess of protein is removed by repeated centrifugation and washing of the sediment with fresh buffer. After completion of the washing procedure, the latex particles are re-suspended in an aqueous medium which preferably contains an inert protein, e.g. bovine serum albumin, in order to protect the particles from non-selective interactions with non-specific proteins of the test samples.

If desired, the proteins can also be bound covalently to the latex particles following the procedure described in U.S. Pat. No. 3,857,931 using a water soluble carbodiimide coupling agent.

The determinations to be made according to the method of this invention may be performed homogeneously or heterogeneously. Homogeneous determinations are particularly simple to perform but require a measurable change of the perceived signal arising from either those latex particles present in the labelled reagent or in the labelled complex formed between the labelled reagent and the particles to be determined. In those instances where no such distinction is possible, heterogeneous determinations will have to be performed.

Homogeneous determinations are advantageous due to the fact that it is not necessary to physically separate the bound and unbound labelled species, thus reducing the number of steps necessary to perform an assay. The reaction between the labelled component and the corresponding binding counterpart causes the measurable change in the label's participation in or modulation of the signal generating moiety necessary to perform a homogeneous determination. The distribution of the latex particles between the bound and unbound species may be differentiated by the inability or altered ability of the said latex particles to affect the signal arising therefrom when present in the bound species.

A homogenous determination may conveniently be performed according to art-known procedures such as, for example, the competitive binding technique. There, the sample containing the analyte is combined with a binding counterpart of the analyte, a labelled reagent comprising a latex particle coupled to the analyte or a specific binding analogue thereof, and if necessary, the other components necessary to convert the precursor of the signal generating moieties in the latex particle to the signal generating moiety itself. Alternatively, a sequential determination may be performed whereby the sample and the analyte binding counterpart are first combined and thereafter the detectant reagent added.

The determination of antibiotics or other binding proteins, receptors, antibodies having specificity for a particular antigen or hapten or binding materials in general can also be performed following a direct technique. The liquid medium containing the component to be detected is combined with a labelled reagent comprising a latex particle coupled to a binding counterpart of the analyte and, if necessary, the other components to convert the precursor of the signal generating moieties in the latex particle to the signal generating moieties themselves, whereafter the sisal arising from the latex particles which is altered due to the binding, is measured.

In many instances it is not possible to perform homogeneous determinations. In these cases a heterogeneous determination can be a particularly attractive alternative. In general a heterogeneous determination system comprises three basic constituents which are combined simultaneously or subsequently, i.e. the analyte to be detected, a binding counterpart of the analyte and the labelled reagent, where necessary along with other components necessary to convert the precursor of the signal generating moiety in the label to the signal generating moiety itself. If necessary after an appropriate incubation period or periods the labelled reagent becomes bound to the particles to be detected whereby the ratio of the bound species to the unbound species is a function of the amount of analyte being present. The bound and unbound species are physically separated and the amount of label being present in one thereof is determined.

Various means of performing the separation step and of performing the binding reactions are known in the art. The said separation may involve conventional techniques such as, for example, by employing a solid-phase antibody or antigen, a second antibody, or a solid-phase second antibody; or by the use of immuno complex precipitation agents, adsorbents, etc. The said binding reactions may for example include the so-called competitive binding technique, the sequential saturation technique, the "sandwich technique", etc.

The preferred determinations to be made according to the method of this invention are heterogeneous determinations which are generally based on the principle that the labelled complex formed between the specific binding protein and the bindable substances is at some time immobilized in such manner that any un-reacted particles can be washed off, whereupon the immobilized particles are detected in situ or, if desired, after disengagement in any other phase derived therefrom.

In a particularly preferred embodiment, the bindable substance to be detected, which may be contained in a crude test specimen or in a purified or partly purified fraction derived therefrom, is immobilized on an appropriate immobilizing support prior to its complexing with the labelled binding protein, specific to said bindable substance.

The immobilization of the bindable substance may be carried out following the usual techniques, e.g. by spotting an aliquot of the test specimen on the immobilizing support or by immersing the latter in the test sample and subsequently drying and optionally washing off non-immobilized material. This is the so-called direct technique. As immobilizing supports for this technique use can be made of various materials, in general polymeric materials like, nitrocellulose, diazobenzyloxymethyl (DBH)- and diazophenylthioether (DPT) modified cellulose paper, paper, paper or cellulose acetate activated with cyanogen bromide, agarose, nylon, plastics, etc. which may take any form which is convenient for the determination process, e.g. sheets, beats, welled plates, dip-sticks, etc.

The support is then brought into contact with a suspension of the coloured or colourable latex particles coated with the specific binding protein under conditions which allow complex formation between the binding protein and the corresponding bindable substances. It has been found that the selectivity can be substantially improved when the support is prior to contacting it with the latex, treated with a surface active agent like, for example, a polyoxyethylene fatty acid ester (e.g. Tween®). Consequently, at the sites where the bindable substance is immobilized, coated latex particles will be immobilized in turn in amounts proportional to the concentration of the immobilized bindable substance.

In a variant of this method, the immobilized bindable substance is first allowed to react with a first binding protein which is specific therefor and subsequently the thus immobilized fase is brought into contact with the coloured or colourable particles coated with a second binding protein which is specific for said first binding protein.

Because of the lack of selectivity and specificity of the immobilizing process as described above, the direct method is usually employed with relatively pure or purified test samples or fractions. For more complex samples, the direct method will often be less suitable, as the non-specific immobilization of a large excess of non-desired material will interfere with the sensitivity and specificity of the determination.

In order to avoid this problem, which is particularly important with regard to routine analyses, use is very often made of an indirect or so-called sandwich technique. In this technique, a purified or enriched primary specific binding protein is immobilized on a solid support. The latter is contacted with the test sample under conditions which allow the complexing of the corresponding bindable substances, which consequently become immobilized themselves. After removal of the test sample and washing of the support, the latter is contacted with a suspension of coloured or colourable latex particles coated with secondary specific binding proteins which are able to bind to uncomplexed sites of the immobilized bindable substance.

The detection of the coloured or colourable latex particles is both convenient and simple. When the particles are already coloured their presence can be observed visually, optionally using a microscope or optionally using a colorimeter or spectrophotometer. Colorimetric or spectrophotometric determinations will be preferred when quantitative determinations are desired. The coloured signal can be observed at the binding side itself or, after disengagement, in the resulting suspension or any fraction or phase derived therefrom.

When colourable particles are used instead, it will be necessary to convert them prior to the evaluation into the corresponding coloured particles by allowing them to react with the particular reagents known to be effective for effecting such conversion. When colour couplers of the type described hereinabove are used, it will be appropriate to contact the particles first with a strong oxidant, such as a peroxide, perborate, peroxoic acid or preferably persulfate and thereafter with a photographic developer, e.g. a phenylene diamine.

The specific binding proteins which can be employed in the method according to the invention can be of various natures but will in many instances be antibodies to specified antigens or haptens. As an example of specific binding substances other than antibodies there can be mentioned lectins, which specifically bind glycoproteins and staphylococcus protein A which specifically binds immunoglobulins of various animal species. Antibodies may be polyclonal or monoclonal, the latter having the advantage of being more specific.

The binding reaction will in almost all cases be allowed to proceed under mild conditions. The reaction mixture will in general be an aqueous medium with any desirable organic cosolvents being present in minor amounts. The temperature of the reaction will be maintained at a constant level in normal circumstances throughout the incubation period and the enzyme measurement step. Temperatures will generally be between 5° and 50° C., more usually between 20° and 40° C. Preferably the reaction will proceed at room temperature. The pH of the reaction mixture will vary between 5 and 10, more usually between 6 and 9. The concentration of various reagents will depend on the level of analyte expected in the test medium, with such level usually being between $10^{-3}$ and $10^{-12}$M. As in the case of the previously described reaction parameters, selection is primarily based on empirically derived optimization balanced against the preferences and needs of the technician who whill ultimately perform assays on a routine basis. None of the parameters therefore is of a critical nature to the present invention, rather they are all within the ordinary ranges used in the art.

In view of its general nature, the method according to the invention has an extremely wide field of application. In principle it can be applied to the detection and/or quantitative determination of any substances for which specific binding proteins exist. For example, such substances comprise but are not limited to cell surface and tissue antigens, biological substances excreted by or derived from living organisms, particularly biological substances occurring in biological fluids such as saliva, lymph, blood and its derived fractions such as, plasma and serum, urine, cerebrospinal fluid, amnion fluid, etc. Substances which can be detected include, proteins, polypeptides, peptides, like enzymes, hormones, structural proteins nucleic acids; vitamins; polysaccharides toxins; alkaloids: glycoproteins; haptens; metabolites; pharmacological agents; steroids, and any other molecules for which a specific binding counterpart exists in biological systems or can be synthesized.

Representative protein analytes include the classes of protamines, mucoproteins, glycoproteins, globulins, albumins, scleroproteins, phosphoproteins, histones, lipoproteins, chromoproteins, and nucleoproteins. Examples of specific proteins are prealbumin, $\alpha_1$-lipoprotein, human serum albumin, $\alpha_1$-acid glycoprotein, $\alpha_1$-antitrypsin, $\alpha_1$-glycoprotein, transcortin, thyroxine binding globulin, haptoglobin, hemoglobin, myoglobin, ceruloplasmin, $\alpha_2$-lipoprotein, $\alpha_2$-macroglobulin, $\beta$-lipoprotein, erythroprotein, transferin, hemopexin, fibrinogen, the immunoglobulins such as IgG, IgM, IgA, IgD, and IgE, and their fragments, e.g., $F_c$ and $F_{ab}$, complement factors, prolactin, blood clotting factors such as fibrinogen, thrombin and so forth, insulin, melanotropin, somatotropin, thyrotropin, follicle stimulating hormone, luteinizing hormone, gonadotropin, thryroid stimulating hormone, placental lactogen, intrinsic factor, transcoblaamin, serum enzymes such as alkaline phosphatase, lactic dehydrogenase, amylase, lipase, phosphatases, cholinesterase, glutamic oxaloacetic transaminase, glutamic pyruvic transaminase, and uropepsin, endorphins, enkephalins, protamine, tissue antigens, bacterial antigens, and vital antigens such as hepatitis associated antigens (e.g., $HB_sAg$, $HB_cAg$ and $HB_eAg$).

Representative hapten analytes include the general classes of drugs, metabolites, hormones, vitamins, and the like organic compounds. Haptenic hormones include thyroxine and triidothyronine. Vitamins include vitamins A, B, e.g., $B_{12}$, C, D, E and K, folic acid and thiamine, Drugs include antibiotics such as aminoglycosides, e.g., gentamicin, tobramycin, amidacin, sisomicin, kanamycin, and netilmicin, penicillin, tetracycline, terramycin, chloromycetin, and actinomycetin: nucleosides and nucleotides such as adenosine diphosphate (ADP) adenosine triphosphate (ATP), flavin mononucleotide (FMN), nicotinamide adenine dinucleotide (NAD) and its phosphate derivative (NADP), thymidine, guanosine and adenosine: prostaglandins; steroids such as the oestrogens, e.g., oestriol and oestradiol, steroids: and others such as phenobarbital, phenytoin, pirimidone, ethosuximide, carbamazepine, valproate, theophylline, caffeine, propranolol, procainamide, quinidine, amitryptiline, cortisol, desipramine, disopyramide, doxepin, doxorubicin, nortryptiline, methotrexate, imipramine, lidocaine, N-acetyl-procainamide, amphetamines, catecholamines, and antihistamines. Further cardiac glycosides, and derivatives of benzodiazepine, benzimidazole, piperidine, piperazine, imidazole, triazole, pyridazine, 1,2,4-triazinedione or 2,3,5,6-tetrahydro-imidazo[2,1-b]thiazoles, or amides, hydratropic acid derivatives or trialkylamines.

Benzimidazole derivatives comprise thiabendazole, fuberidazole, ciclobendazole, oxibendazole, parbendazole, cambendazole, mebendazole, fenbendazole, flubendazole, albendazole, oxfendazole, nocodazole and astemizole.

Piperidine derivatives comprise diphenoxylate, phenoperidine, haloperidol, haloperidol decanoate, bromperidol decanoate, bromperidol, moperone, trifluperidol, pipamperone, piritramide, fentanyl, benperidol, droperidol, benzitramide, benzetimide, domperidone, sufentanil, carfentanil, alfentanil, dexetimide, milenperone, difenoxin, fluspirilene, penfluridol, pimozide, lorcainide, loperamide, astemizole, ketanserine, levocabastine, cisapride, altanserin, titanserin, 3-[2-[4-(4-fluorobenzoyl)-1-piperidinyl]ethyl]-2,7-dimethyl-4H-pyrido[1,2-a]pyrimidin-4-one, 3-[2-[4-[bis(4-fluorophenyl)methylene]-1-piperidinyl]ethyl]-2-methyl-4M-pyrido[1,2-a]pyrimidin-4-one and 3-[2-[4-[[3-(2-furanylmethyl)-3H-imidazo[4,5-b]pyridin-2-yl]amino]-1-piperidinyl]ethyl]-2-methyl-4H-pyrido[1,2-a]pyrimidin-4-one.

Piperazine derivatives include azaperone, fluanisone, lidoflazine, flunarizine, mianserine, oxatomide, mioflazine, clocinizine and cinnarizine.

Examples of imidazole derivatives are metronidazole, ornidazole, ipronidazole, tinidazole, isoconazole, nimorazole, miconazole, burimamide, metiamide, metomidate, enilconazole or imazalil, etomidate, econazole, clotrimazole, carnidazole, cimetidine, doconazole, sulconazole, parconazole, orconazole, butoconazole, triadiminole, tioconazole, valconazole, fluotrimazole, ketoconazole, oxiconazole, lombazole, bifonazole, oxmetidine, fenticonazole, tubulazole and (Z)-1-[2-chloro-2-(2,4-dichlorophenyl)ethenyl]-1H-imidazole.

Triazole derivatives comprise virazole, azaconazole, etaconazole, propiconazole, penconazole, itraconazole and terconazole.

Pyridazine derivative comprise for example, 3-chloro-6-[3,6-dihydro-4-(3-methylphenyl)-1(2H)-pyridinyl]pyridazine, 3-methoxy-6-[4-(3-methylphenyl)-1-piperazinyl]pyridazine and the compounds of Publ. Eur. Pat. Appl. No. 0,156,433.

1,2,4-Triazinediones comprise for example, 2-chloro-α-(4-chloro-phenyl)-4-(4,5-dihydro-3,5-dioxo-1,2,4-triazin-2(3H)-yl)benzeneacetonitrile, 2,6-dichloro-α-(4-chlorophenyl)-4-(4,5-dihydro-3,5-dioxo-1,2,4-triazin-2(3H)-yl)benzeneacetonitrile and the compounds of Publ. Eur. Pat. Appl. No. 0,170,316.

Trialkylamines are, for example, diisopromine, prozapine. 2,3,5,6-Tetrahydro-imidazo[2,1-b]thiazoles comprise, for example, tetramisole or levamisole.

Amides comprise for example, closantel, ambucetamide, isopropamide, buzepide metiodide, dextromoramide.

A hydratropic acid derivative is, for example, suprofen.

The purposes of the determinations can be multiple. In certain applications they will be used merely as a scientific tool, to visualize particular substances, e.g. on histological coupes, on chromatograms, electrophoretograms, blots, etc. For example, when applying different lables to different specific proteins or other bindable substances on a chromatogram, electrophoretogram, protein blot etc., a reference pattern is obtained which can advantageously be used to localize other proteins or other substances. Apart from its scientific utility, the method of the invention will find utility in a wide variety of diagnostic tests such as, for example, the following: the detection and characterisation of subpopulations of T-lymphocytes; pregnancy tests based on the presence of certain hormones (choriotrophic gonadotropin) in the urine, diagnostic tests for various infections diseases of i.a. fungal, bacterial and in particular vital origin, such as, for example, hepatitis B, auto-immune-diseases (AIDS), gonorrhoea, rubella, poliomyelitis, etc.

Hence it can be employed in virtually all circumstances for which immunological techniques are conceived at present.

Diagnostics for metabolic, endocrinological and various endogenous diseases, including diagnostics for the detection of congenital malfunctions of embryo's based on the presence of specific proteins in the amnion fluid.

Since the latexes for use in the method according to the invention occur in different colours, multivalent diagnostics can be prepared which allow the simultaneous detection and/or determination of more than one bindable substance.

In view of its simplicity and ease of operation, the method lends itself particularly for routine tests, not only for use by specialists and technicians in the laboratory, but also for use by laymen who have no skills in the relevant technical field. The method can also be easily automated which is an important factor when large numbers of identical determinations must be carried out, e.g. in blood banks and specialized clinical laboratories.

Coloured and colourable latex particles coated with specific binding proteins are deemed to be novel and as useful tools in the method according to the invention they constitute an additional feature thereof. The invention further comprises reagent systems which comprise all of the essential chemical elements required to conduct a desired assay method encompassed by the present invention. The reagent system is presented in a commercially packaged form, as a composition or admixture where the comparability of the reagents will allow, in a test device configuration, or as a test kit, i.e., a packaged combination of one or more containers holding the necessary reagents. Included in the reagent system are the reagents appropriate for the binding reaction system desired, always requiring a labelled reagent and the other components necessary to produce the signal-generating reaction. Such binding reaction reagents can include, in addition to the labelled reagent, a binding counterpart to the analyte, and so forth. Of course, the reagent system can include other reagents as are known in the art and which may be desirable from a commercial and user standpoint, such as buffers, diluents, standards, and so forth.

More preferably the invention comprises test kits for the qualitative or quantitative determination of specific bindable substances which comprise, besides other reagents, an aqueous suspension of latex particles which are coated with specific binding proteins to said bindable substances or to primary specific binding proteins to said bindable substances.

The method is further illustrated by the following examples which are not intended to limit the scope of the invention.

Materials

The suspensions of the colour coupler latexes $M_1$, $C_2$ and $Y_1$ used in these examples have the following compositions:

|  | % of emulsifier (1) | g of used polymer /100 g | mmol of colour coupler /100 g of latex |
|---|---|---|---|
| $M_1$ (2) | 3.2 | 22 | 36.5 |
| $C_1$ | 5.6 | 23.5 | 36 |
| $C_2$ | 2.2 | 20 | 31.5 |
| $Y_1$ | 5.4 | 19.3 | 21 |

(1) % of wetting agent (N-methyl- or N-oleylmethyltauride) expressed in grams per 100 grams of polymer.
(2) M: Magenta, C: Cyan, Y: Yellow.

Composition of the polymers:

$M_1$: co[2-methyl-N-(1-phenyl-5-oxo-2-pyrazolin-3-yl)-acrylamide/butyl acrylate]

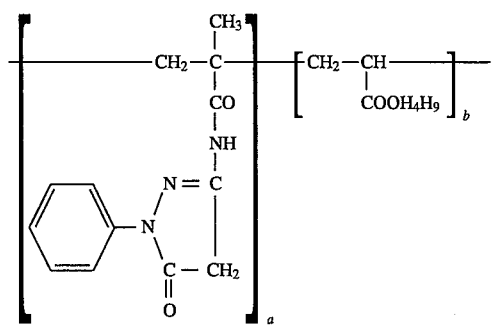

a = 40% weight, b = 60% weight $C_1$: co[butyl acrylate/2-methacryloylamido-5-methylsulphonyl-aminophenyl]

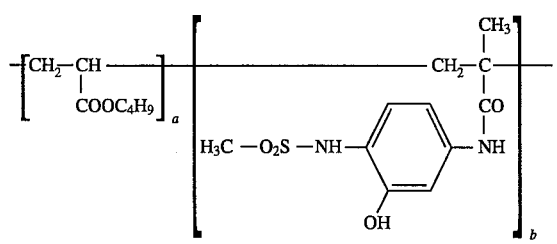

a = 59% weight, b = 41% weight $C_2$: co[butyl acrylate/methacrylic acid/N-(3,5-dichloro-4-methyl-6-hydroxy)-phenyl-methacrylamide]

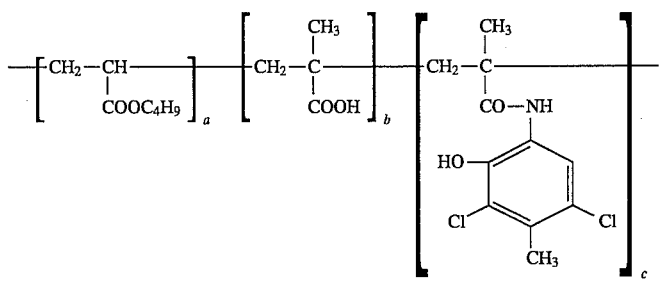

a = 49% weight, b = 10% weight, C = 41% weight $Y_1$: co[2-pivaloyl-2-chloro-2'-chloro-5'-methacryloylaminoacetanide/butyl acrylate/methacrylic acid]

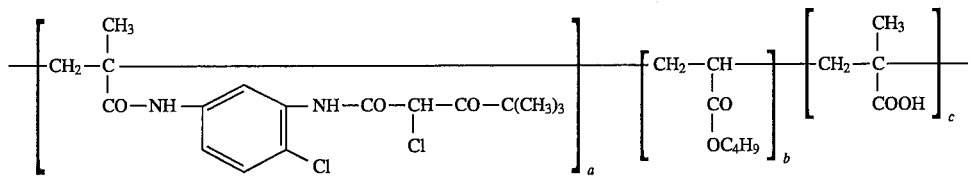

a = 40% weight, b = 29% weight, c = 31% weight

EXAMPLE 1

Preparation of latex bound antibodies

A suspension of colour coupler latex $M_1$, $C_2$ and $Y_1$ was diluted to a 2% (polymer content) suspension using a sodium carbonate dilution buffer (0.015M $Na_2CO_3$, 0.035M $NaHCO_3$, 0.2 g/l $NaN_3$, pH 9.3). A protein (antibody) solution, containing 0.5 mg/ml affinity-purified goat anti-mouse immunoglobulin was added to 5 ml of the latex suspension.

This mixture was stirred for 17 hours at room temperature. After adsorption of the antibodies to the latex, the unbound antibodies were removed by centrifugation (60 min, 25000 g, 4° C.). The precipitate which contained the latex particles was re-suspended in a 2 ml 0.1 molar solution of sodium phosphate (pH 7.5) by pressing it through a syringe. Free active binding sites on the latex were coated by adding a 10 ml of a 5% (w/v) bovine serum albumin solution (BSA) in 0.05M sodium phosphate solution (pH 7.5) and subsequent incubation for 30 min at 37° C. The mixture was centrifuged (60 min, 25.000 g, 4° C.) and the precipitate containing the latex was re-suspended as described above in 10 ml of an aqueous solution of 0.05M sodium phosphate—5g/l BSA—5 ml/l Tween 20®—0.5 g/l $NaN_3$ and stored at 4° C.

Performance test of coupled latex

Latex-antibody complexes were reacted with antigen which was fixed to a nitrocellulose membrane.

To measure sensitivity, a dilution series of the antigen was made in a buffer consisting of 0.02M Tris(hydroxymethyl)aminoethane—0.15M NaCl— 0.5 g/l $NaN_3$, $NaN_3$ (pH 8.2, with HCl) with 50 μg/ml albumin as carrier. A concentration series of 250 - 125 - 62.5 - 31 - 15.5 - 7.75 - 3.9 - 1.9 - 0.8 and 0.4, ng/μl was prepared and 1 μl thereof was spotted onto nitrocellulose strips (0.6×6 cm).

Subsequently, the thus treated nitrocellulose strips were treated with 0.05M sodium phosphate (pH 7.5)—5% (v/v) Tweene solution for 30 minutes at 37° C., and subsequently washed three times with water for 10 min.

The nitrocellulose strips were incubated for 2–3 hours with the latex suspension, prepared as mentioned above. They were washed three times with water and immersed for a few seconds in a 10% potassium persulfate solution and put in a developer solution containing 4-(N-butyl, N-ω-sulfobutyl)amino-aniline as developing agent till sufficient colour was visible.

As a control the same quantities of albumin, instead of immunoglobulin (antigen), were in the same way spotted.

Results a. Determination of the quantity of antibodies needed to coat the latex

The optimal concentration of protein (antibodies) to be coupled to the latex was determined in the following test procedure. A series of solutions of various concentration, (antibody concentrations of 2 - 1 - 0.5 - 0.1 mg/ml) was added to 5 ml of the 2% latex suspension. The thus obtained mixtures were further treated following the same described hereinabove. The colour intensities obtained with the latex-antibody complexes prepared with the various concentrations of antibody were compared. It appeared that the optimal concentration of antibodies was 0.5 mg/ml since higher concentrations gave no increase of colour intensity of the spots, lower concentrations gave less intensity.

b. Sensitivity

The detection sensitivity is defined as the minimal detectable spot in the antigen dilution series. This sensitivity varies with the type of latex. In a typical experiment the following sensitivities were found: colour coupler latex $M_1$ 1.9 ng/μl; colour coupler latex $Y_1$ 15.5 ng/μl; colour coupler latex $C_2$ 7.7 ng/μl.

c. Specificity

Coloured spots were detected when replacing the antigen by bovine serum albumin in the previous experiments, which proves the specificity of the method.

EXAMPLE 2

Design of a dip-stick test for the simultaneous determination of rheumatoid factor and C-reactive protein in undiluted human serum

Preparation of the anti-rheumatoid factor colour-coupled latex

A suspension of colour coupler latex $C_1$ was diluted to 2% (polymer content) in a sodium carbonate dilution buffer (0.015M $Na_2CO_3$, 0.035M $NaHCO_3$, 0.2 g/l $NaN_3$, pH 9.3). 125 mg normal human immunoglobulin dissolved in 5ml of the aforementioned carbonate buffer were mixed with 250 ml of the diluted latex suspension. This mixture was stirred overnight at room temperature to allow the immunoglobulin to adsorb on the latex beads.

In order to block the free active binding sites on the latex, 100 ml of a 5% (w/v) bovine serum albumin (BSA) solution in a 50 mM phosphate buffer at pH 7.5 were added to the stirred mixture which was then put at 37° C. for 30 min. The remaining unbound immunoglobulin and BSA were washed away from the latex particles with phosphate-BSA-Tween®-NaCl buffer (0.05M sodium phosphate, 5 g/l BSA, 5 ml/l Tween 20®, 1M NaCl, 0.5 g/l $NaN_3$, pH 7.5). The latex suspension was then brought at the original volume of 250 ml in the same phosphate-BSA-Tween®-NaCl buffer.

Preparation of the anti-C-reactive protein colour-coupled latex

A suspension of colour coupler latex $M_1$ was diluted to 2% (polymer content) in the carbonate buffer described hereinabove. 2 ml of anti-C-reactive protein (anti-CRP) antibodies (39.6 mg/ml), were mixed with 250 ml of the diluted latex suspension. This mixture was stirred overnight at room temperature.

The latex particles were washed in glycin-Triton-SDS® buffer (0.1M glycin, 0.1M NaCl, 0.12 mg/ml NaOH, 1 g/l $NaN_3$, 1 ml/l Triton X705® 50%, 14 mg/l sodium dodecyl sulphate (SDS). Afterwards, the suspension was diluted ten times in a 50 mM phosphate buffer (pH 7.5) containing 5% (w/v) BSA, and kept at 37° C. for 30 min. The latex particles were then washed in the phosphate-BSA-Tween®-NaCl buffer described hereinabove. During this process, the volume of the latex suspension was reduced to the original 250 ml.

Preparation of the CNBr-activated paper 20 g of filter paper were washed for 3 min in excess water. 20 g CNBr were dissolved in 600 ml water. The filter paper was put in the CNBr solution which was immediately brought at a pH between 10.5 and 11 with NaOH. The paper was allowed to react for 30 min under constant monitoring of the pH of the CNBr solution, adjusting it when necessary. Afterwards, the paper was washed successively in 5 1 0.5 mM $NaHCO_3$, 500 ml water (twice), 500 ml 25% acetone (twice), 500 ml 50% acetone (twice), 500 ml 75% acetone (twice) and 500 ml 100% acetone. The activated filter paper was then air-dried and stored at −20° C.

Preparation of anti-rheumatoid factor and anti-CRP specific paper 1 g of CNBr-activated paper was put in 40 ml 0.1M $NaHCO_3$ containing 60 mg human immunoglobulin for 3 h at 4° C. The paper was then washed successively in 100 ml 1 mM $NaHCO_3$ for 10 min, in 100 ml 0.1M glycin for 2 h, in 100 ml 1 mM $NaHCO_3$ for 10 min (twice), in 100 ml 0.1M Na-acetate (pH 4) for 30 min and in 100 ml phosphate-BSA-Tween® buffer (0.05M sodium phosphate, 5 g/l BSA, 5 ml/l Tween® 20, 0.5 g/l $NaN_3$, pH 7.5) for 10 min. The human immunoglobulin-containing paper was then stored overnight in this phosphate-BSA-Tween® buffer at 4° C.

The same procedure was followed for the attachment of anti-CRP antibodies to CNBr-activated paper.

Assembly of the dip-stick

Sticks (5×100 mm) were made out of 0.2 mm polyester sheets. One 5×5 mm human immunoglobulin-containing piece of filter paper and one 5×5 mm anti-CRP antibody-containing piece of filter paper were glued next to each other, close to one edge of the stick. Care was taken to leave a 1 mm gap between both pieces of paper. The glue was allowed to dry at room temperature overnight. The assembled dip-sticks were stored at 4° C.

Performance of the test 0.5 to 1 ml of a patient's serum was put in a 10 ml polystyrene test tube. The dip-stick was added for 30 to 60 min in a way that both activated sites were properly immersed. The dip-stick was then washed with running tap water for about 10 s. Afterwards, the stick was put in a mixture of 1 ml anti-CRP colour coupled latex and 1 ml anti-rheumatoid factor colour coupled latex for 30 to 60 min. Then, the dipstick was washed again with tap water and held for a few seconds in a 10% persulfate solution. As a final step, the colour was developed by immersing the stick for about five seconds in a developer containing 4-(butyl,N-ω-sulfobutyl)amino-aniline as developing agent.

Evaluation of the test

Several human sera were tested with the procedure described above.

All sera were first checked with commercial latex agglutination tests to classify them as rheumatoid factor-positive or -negative or as CRP-positive or -negative. The rheumatoid factor-positive sera generated a clear blue signal on the dispstick whereas rheumatoid factor-negative sera did not generate any signal at all. CRP-positive sera generated a dark red signal which could easily be distinguished from the faint red signal generated by a CRP-negative signal. This faint signal can be attributed to the presence of low levels of CRP in healthy individuals.

What we claim is:

1. A method of qualitatively or quantitatively determining a component of a complex formed between at least one specific binding protein and its corresponding bindable substance which comprises labeling at least one component of said complex with a marker characterized in that the marker used consists of colored latex particles which comprise recurrent units of monomer carrying a moiety which is oxidatively coupled with an amino compound to form a dye and the determination is based on the color characteristics of the colored particles derived therefrom.

2. A method according to claim 1 wherein the said colored latex particles comprise recurrent units of a monomer represented by the formula:

wherein:

R is hydrogen, halogen or $C_{1-4}$ alkyl;

Q is a color coupler group which is oxidatively coupled with an aromatic primary amino compound.

3. A method according to claim 2 wherein the aromatic primary amino compound is a p-phenylene diamine and Q is phenol, napthol, pyrazolone, indazolone or acylacetamide or a derivative thereof.

4. A method according to claim 1 wherein the colored latex comprises a polymer of the formula:

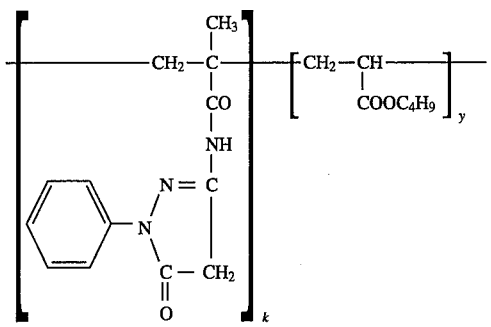

wherein k is from 30 to 60 w/w and y is from 40 to 70 w/w, which is oxidatively coupled with a p-phenylene diamine; or of the formula:

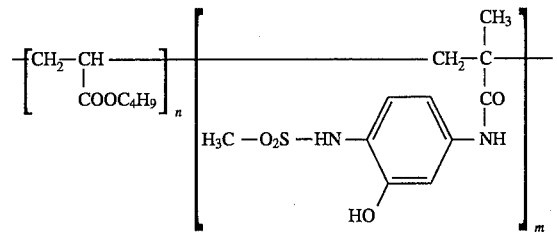

wherein n is from 40 to 70 w/w and m is from 30 to 60 w/w, which is oxidatively coupled with a p-phenylene diamine.

5. Colored latex particles coated with a specific binding protein wherein the particles comprise a polymer containing recurrent units of a monomer represented by the formula:

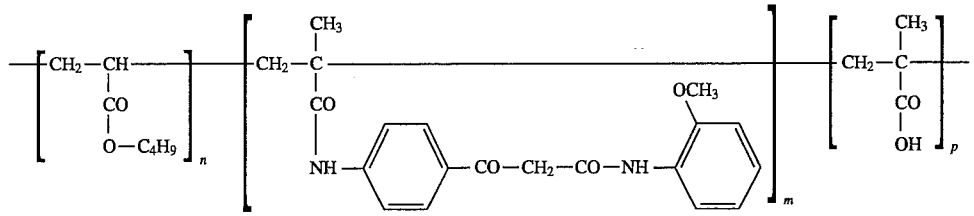

wherein n is from 20 to 70 w/w, m is from 30 to 60 w/w, and p is from 0 to 40 w/w, which is oxidatively coupled with a p-phenylene diamine; or of the formula:

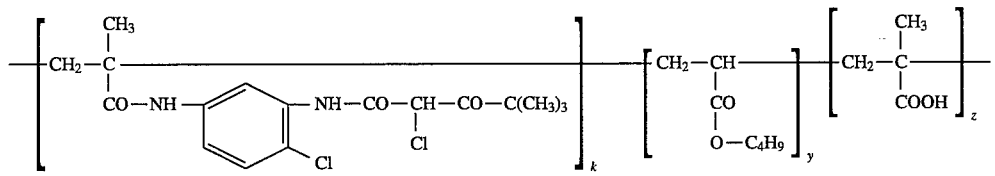

wherein k is from 30 to 60 w/w, y is from 20 to 70 w/w, and z is from 0 to 40 w/w, which is oxidatively coupled with a p-phenylene diamine; or of the formula

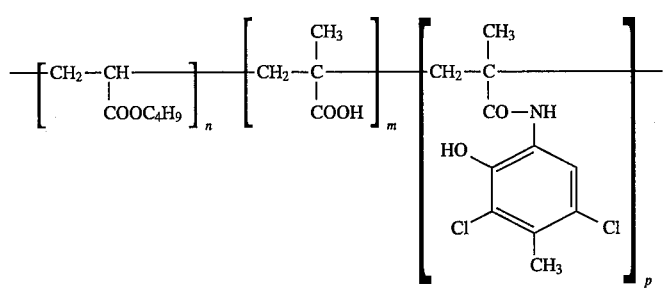

wherein n is from 20 to 70 w/w, m is from 0 to 40 w/w, and

wherein:

R is hydrogen, halogen or $C_{1-4}$ alkyl;

Q is a color coupler group which is oxidatively coupled with an aromatic primary amino compound.

6. Colored latex particles according to claim 5 wherein the aromatic primary amino compound is a p-phenylene diamine and Q is phenol, naphthol, pyrazolone, indazolone or acylacetamide or a derivative thereof.

7. Colored latex particles according to claim 5 wherein the colored latex comprises a polymer of the formula:

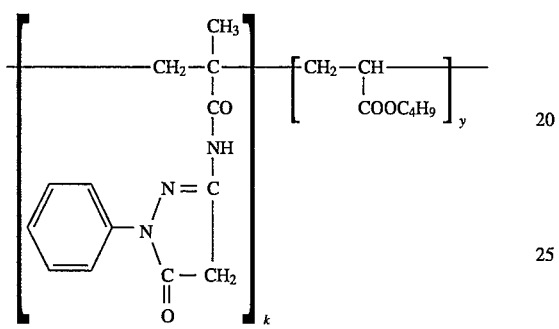

wherein k is from 30 to 60 w/w and y is from 40 to 70 w/w, which is oxidatively coupled with a p-phenylene diamine; or of the formula:

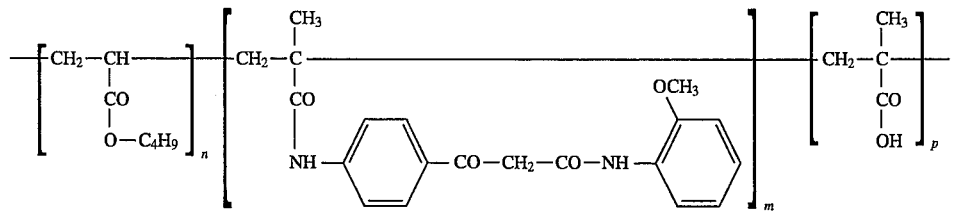

wherein n is from 20 to 70 w/w, m is from 30 to 60 w/w, and p is from 0 to 40 w/w, which is oxidatively coupled with a p-phenylene diamine; or of the formula:

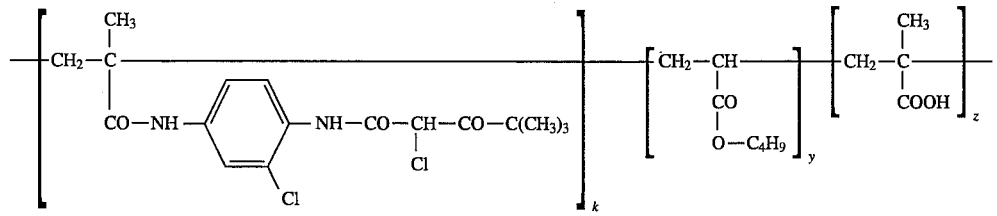

wherein k is from 30 to 60 w/w, y is from 20 to 70 w/w, and z is from 0 to 40 w/w, which is oxidatively coupled with a p-phenylene diamine; or

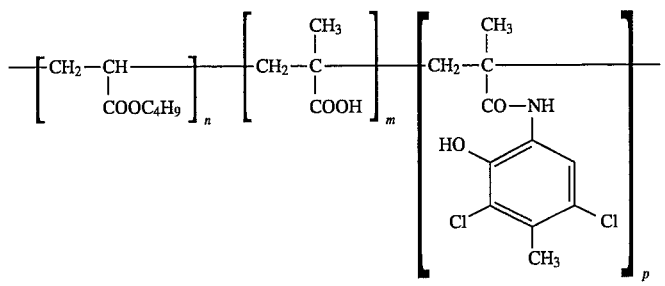

wherein n is from 20 to 70 w/w, m is from 0 to 40 w/w, and p is from 30 to 60 W/w, which is oxidatively coupled with a p-phenylene diamine; or of the formula:

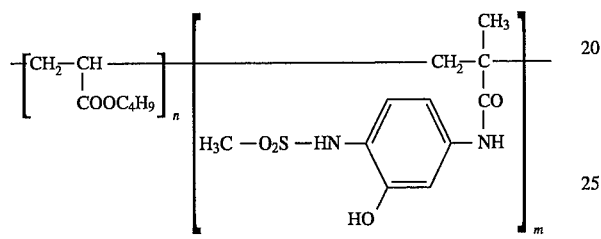

wherein n is from 40 to 70 w/w and m is from 30 to 60 w/w, which is oxidatively coupled with a p-phenylene diamine.

8. A method according to claim 1, comprising the steps of:
   a) immobilizing the bindable substance on a solid support;
   b) contacting the support containing the immobilized bindable substance with an aqueous suspension of colored latex particles coated with binding proteins specific to said bindable substance; and
   c) observing the degree of color formation on said solid support and relating said color formation to the presence of said bindable substance.

9. A method according to claim 8, wherein the said bindable substance is immobilized on the said solid support by allowing the said bindable substance to be bound by a specific binding protein which is immobilized on the said solid support.

10. A method according to claim 1, comprising the steps of:
    a) immobilizing the bindable substance on a solid support;
    b) contacting the support containing the immobilized bindable substance with a first binding protein specific to said bindable substance to form a complex herewith;
    c) treating the support carrying the thus formed complex with an aqueous suspension of colored latex particles coated with a secondary binding protein which is specific to the said first binding protein; and
    d) observing the degree of color formation on said solid support and relating said color formation to the presence of said bindable substance.

11. A test kit for the determination of a particular bindable substance which comprises the particles of claim 5 and ancillary reagents.

12. A test kit for the determination of a particular bindable substance which comprises a primary binding protein which is specific to said bindable substance and the particles of claim 5 in which the specific binding protein is specific to the primary binding protein.

* * * * *